(12) United States Patent
Foster

(10) Patent No.: US 7,270,700 B2
(45) Date of Patent: Sep. 18, 2007

(54) MAGENTA DYES AND INKS FOR USE IN INK-JET PRINTING

(75) Inventor: Clive Edwin Foster, Manchester (GB)

(73) Assignee: Fujifilm Imaging Colorants Limited, Manchester (GB)

( * ) Notice: Subject to any disclaimer, the term of this patent is extended or adjusted under 35 U.S.C. 154(b) by 63 days.

(21) Appl. No.: 11/292,001

(22) Filed: Dec. 2, 2005

(65) Prior Publication Data

US 2006/0117990 A1 Jun. 8, 2006

(30) Foreign Application Priority Data

Dec. 2, 2004 (GB) .................................. 0426494.1

(51) Int. Cl.
  *C09D 11/00* (2006.01)
  *C09D 11/02* (2006.01)
  *C07C 50/36* (2006.01)
  *B41J 2/01* (2006.01)

(52) U.S. Cl. ................................ 106/31.27; 106/31.43; 552/284; 347/100

(58) Field of Classification Search ............ 106/31.27, 106/31.43, 31.46, 31.47, 31.49; 552/284; 347/100
See application file for complete search history.

(56) References Cited

U.S. PATENT DOCUMENTS

| | | | | |
|---|---|---|---|---|
| 1,805,913 | A | * 5/1931 | Herz et al. ................... | 552/284 |
| 1,876,972 | A | * 9/1932 | Kunz et al. .................. | 552/284 |
| 1,876,973 | A | * 9/1932 | Kunz et al. .................. | 552/284 |
| 1,897,427 | A | * 2/1933 | Heidenreich ................ | 552/284 |
| 2,191,685 | A | * 2/1940 | Scheyer et al. ............. | 544/248 |
| 2,292,551 | A | * 8/1942 | Stilmar ....................... | 548/437 |
| 2,645,641 | A | * 7/1953 | Renfrew et al. ............ | 546/264 |
| 2,645,645 | A | * 7/1953 | Randall et al. ............. | 552/282 |
| 3,904,650 | A | * 9/1975 | Dokunikhin et al. ....... | 549/232 |
| 4,705,572 | A | * 11/1987 | Spietschka et al. ........ | 106/493 |
| 5,035,747 | A | * 7/1991 | Dietz et al. ................. | 106/495 |

FOREIGN PATENT DOCUMENTS

JP 09122470 A2 5/1997

OTHER PUBLICATIONS

Dalvi et al., "New Dyes from Naphthostyril-5-carboxylic Acid: Synthesis of 6,12-Anthanthrenedione-3,4,9,10-tetracarboxylic Diimides, Naphthostyril-5,6-dicarboximides & 1-Amino-4-arylaminonaphthalene-5,8-dicarboxylic Bislactams", Indian Journal of Chemistry, 24B:377-382 (Apr. 1985).

* cited by examiner

*Primary Examiner*—Helene Klemanski
(74) *Attorney, Agent, or Firm*—Morgan Lewis & Bockius LLP

(57) ABSTRACT

A composition comprising:
(a) a compound of Formula (1)

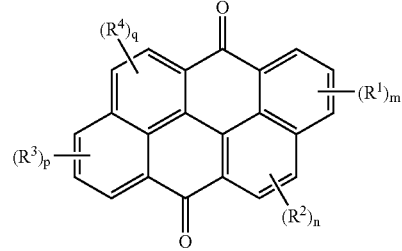

Formula (1)

wherein:
  $R^1$, $R^2$, $R^3$ and $R^4$ independently are substituents;
  m and p independently are 0 to 3; and
  n and q independently are 0 to 2:
provided that the compound of Formula (1) comprises at least one water solubilising group; and
(b) a liquid media.
Also novel compounds and ink-jet printer inks, processes and cartridges.

15 Claims, No Drawings

MAGENTA DYES AND INKS FOR USE IN INK-JET PRINTING

This invention relates to compositions and inks for ink jet printers, to dyes, to printing processes, to printed substrates and to ink-jet printer cartridges.

Ink-jet printing is a non-impact printing technique in which droplets of ink are ejected through a fine nozzle onto a substrate without bringing the nozzle into contact with the substrate. The set of inks used in this technique typically comprise yellow, magenta, cyan and black inks. The colour of the inks in any given ink-set is precisely matched so that when printed in combination they are able to reproduce a full colour spectrum.

With the advent of high-resolution digital cameras and ink-jet printers it is becoming increasingly common for consumers to print off photographs using an ink-jet printer. This avoids the expense and inconvenience of conventional silver halide photography and provides a print quickly and conveniently.

While ink-jet printers have many advantages over other forms of printing and image development there are still technical challenges to be addressed. For example, there are the contradictory requirements of providing ink colorants that are soluble in the ink medium and yet do not run or smudge excessively when printed on paper. The inks need to dry quickly to avoid sheets sticking together after they have been printed, but they should not form a crust over the tiny nozzle used in the printer. Storage stability is also important to avoid particle formation that could block the tiny nozzles used in the printer especially since consumers can keep an ink-jet ink cartridge for several months. Furthermore, the resultant images desirably do not fade rapidly on exposure to light or common oxidising gases such as ozone.

The present invention provides a composition comprising:

(a) a compound of Formula (1)

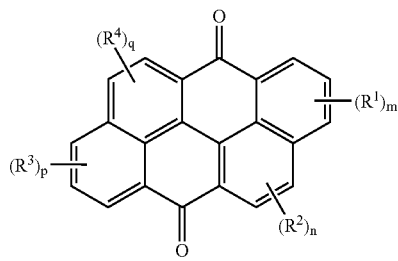

Formula (1)

wherein:

$R^1$, $R^2$, $R^3$ and $R^4$ independently are substituents;
m and p independently are 0 to 3; and
n and q independently are 0 to 2:
provided that the compound of Formula (1) comprises at least one water solubilizing group; and (b) a liquid media.

$R^1$, $R^2$, $R^3$ and $R^4$ are preferably independently selected from: optionally substituted alkyl (preferably $C_{1-4}$-alkyl), optionally substituted alkenyl (preferably $C_{1-4}$-alkenyl), optionally substituted alkynyl (preferably $C_{1-4}$-alkynyl), optionally substituted alkoxy (preferably $C_{1-4}$-alkoxy), optionally substituted aryl (preferably phenyl), optionally substituted aryloxy (preferably phenoxy), optionally substituted heterocyclyl (including heteroaryl), polyalkylene oxide (preferably polyethylene oxide or polypropylene oxide), $CO_2H$, $SO_3H$, $PO_3H_2$, nitro, cyano, halo, ureido, —$SO_2F$, hydroxy, ester, sulphate, —$NR^aR^b$, —$COR^a$, —$CONR^aR^b$, —NHCOR$^a$, carboxyester, sulfone, and —$SO_2NR^aR^b$ wherein $R^a$ and $R^b$ are each independently H or optionally substituted alkyl (especially $C_{1-4}$-alkyl), —S—$R^c$, —O—$R^c$, —NH—$R^c$, wherein $R^c$ is optionally substituted alkyl (preferably $C_{1-4}$-alkyl), optionally substituted alkenyl (preferably $C_{1-4}$-alkenyl), optionally substituted alkynyl (preferably $C_{1-4}$-alkynyl), optionally substituted alkoxy (preferably $C_{1-4}$-alkoxy), optionally substituted aryl (preferably phenyl), optionally substituted aryloxy (preferably phenoxy), optionally substituted heterocyclyl, polyalkylene oxide (preferably polyethylene oxide or polypropylene oxide), Optional substituents for any of the above substituents may be selected from the same list of substituents.

It is preferred that at least one of the groups represented by $R^1$, $R^2$, $R^3$ and $R^4$ and more preferably at least two of the groups represented by $R^1$, $R^2$, $R^3$ and $R^4$ is —S—$R^c$, —O—$R^c$ or —NH—$R^c$ wherein $R^c$ is optionally substituted alkyl (preferably $C_{1-4}$-alkyl) or optionally substituted aryl (preferably phenyl) and especially optionally substituted phenyl and the optional substituents are selected from the list above.

Preferably m, n, p and q are each independently 0 or 1.

Preferably the sum of m+n+p+q is 2.

It is particularly preferred that at least one, and more preferably two of the groups represented by $R^1$, $R^2$, $R^3$ and $R^4$ is/are —S—$R^c$ where $R^c$ is optionally substituted phenyl, where the optional substituents are selected from the list above.

The compulsory water solubilizing group may be bound either directly to the anthanthrone ring system or it may be present as a substituent on one or more of the groups represented by $R^1$, $R^2$, $R^3$ and $R^4$ The water solubilizing group present on the compound of Formula (1) may be any group able to increase the aqueous solubility of the compounds of Formula (1). Thus, for example, it may be an ionisable anionic or cationic group or a non-ionic group such as a polyalkylene oxide.

Preferably the compulsory water solubilizing group is an anionic ionisable group, more preferably the compulsory water solubilizing group is $CO_2H$, $SO_3H$ or $PO_3H_2$.

Preferably the compound of Formula (1) has a solubility in water at 25° C. of at least 1%, more preferably the compound of Formula (1) has a solubility in water at 25° C. of at least 2.5%, it is particularly preferred that the compound of Formula (1) has a solubility in water at 25° C. of at least 5%.

Preferably the compound of Formula (1) is a compound of Formula (2) and salts thereof:

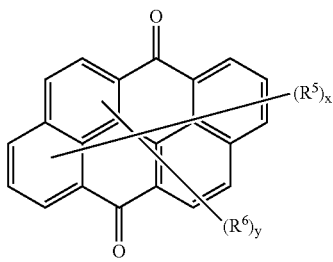

Formula (2)

wherein:
R$^5$ is selected from the group consisting of —S—R$^d$, —O—R$^d$ or —NH—R$^d$ wherein R$^d$ is optionally substituted alkyl (preferably C$_{1-4}$-alkyl), optionally substituted phenyl, optionally substituted naphthyl or optionally substituted heterocycyl;
R$^6$ is a substituent;
x is 1 to 4; and
y is 0 to 9;
provided that the compound of Formula (2) comprises at least one water solubilizing group.

R$^5$ is preferably —S—R$^d$.

R$^d$ is preferably optionally substituted phenyl.

R$^6$ may be selected from the list given for R$^1$, R$^2$, R$^3$ and R$^4$ above.

Preferably x is 1 or 2, more preferably x is 2.

When x is greater than 1 then preferably there is no more than one R$^5$ per component ring.

When x is 2 or 4 then preferably the compound of Formula (2) is a symmetric under a rotation molecule.

Preferably y is 0 to 4, more preferably y is 0.

Thus a particularly preferred molecule of Formula (2) is of Formula (3) and salts thereof:

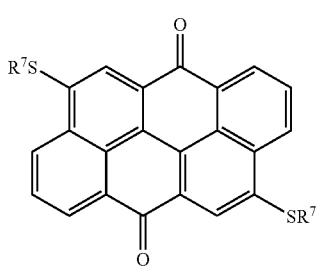

Formula (3)

wherein each R$^7$ is an optionally substituted phenyl and provided that that the compound of Formula (3) comprises at least one water solubilizing group.

Each R$^7$ may vary independently of the other, however it is preferred that each R$^7$ is the same.

The water solubilizing group is as described and as preferred above.

Acid and basic groups on the compounds of Formula (1), particularly acid groups, are preferably in the form of a salt. Thus, the Formulae shown herein include the compounds in free acid and in salt form.

Preferred salts are alkali metal salts, especially lithium, sodium and potassium, ammonium and substituted ammonium salts (including quaternary amines such as ((CH$_3$)$_4$N$^+$) and mixtures thereof. Especially preferred are salts with sodium, lithium, ammonia and volatile amines, more especially sodium salts. The compounds of Formula (1) may be converted into a salt using known techniques.

The compounds of Formula (1) may exist in tautomeric forms other than those shown in this specification. These tautomers are included within the scope of the present invention. However, tautomers may not bear a substituent on the hydroxy/enol oxygen.

Preferred compounds of Formula (1) may be prepared, for Example, by the reaction of a thiophenol derivative and a commercially available compound such as C.I. Vat Orange 3 in the presence of a base.

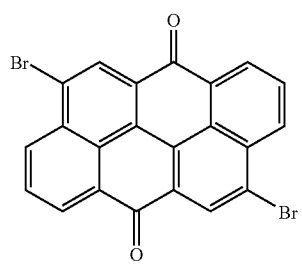

Vat Orange 3

The base must be strong enough to form the anionic aromatic nucleophile. Solvents such as N-methylpyrrolidone are used and vigorous heating is seldom required. Isolation by precipitation is followed by a sulfonation step where the dried dye molecule is typically added to 20% fuming sulfuric acid, and the mixture heated to 50° C. for around 2 hours. Dilution with water is usually enough to effect precipitation of the desired product.

Preferred liquid media include water, a mixture of water and organic solvent and organic solvent free from water. Preferably the liquid media comprises a mixture of water and organic solvent or organic solvent free from water. More preferably the liquid media comprises a mixture of water and organic solvent.

When the liquid medium (b) comprises a mixture of water and organic solvent, the weight ratio of water to organic solvent is preferably from 99:1 to 1:99, more preferably from 99:1 to 50:50 and especially from 95:5 to 80:20.

It is preferred that the organic solvent present in the mixture of water and organic solvent is a water-miscible organic solvent or a mixture of such solvents. Preferred water-miscible organic solvents include C$_{1-6}$alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulfoxides, preferably dimethyl sulfoxide and sulfolane. Preferably the liquid medium comprises water and 2 or more, especially from 2 to 8, water-miscible organic solvents.

Especially preferred water-miscible organic solvents are cyclic amides, especially 2-pyrrolidone, N-methyl-pyrrolidone and N-ethyl-pyrrolidone; diols, especially 1,5-pentane diol, ethyleneglycol, thiodiglycol, diethyleneglycol and triethyleneglycol; and mono-$C_{1-4}$-alkyl and $C_{1-4}$-alkyl ethers of diols, more preferably mono-$C_{1-4}$-alkyl ethers of diols having 2 to 12 carbon atoms, especially 2-methoxy-2-ethoxy-2-ethoxyethanol.

Examples of further suitable liquid media comprising a mixture of water and one or more organic solvents are described in U.S. Pat. Nos. 4,963,189, 4,703,113, 4,626,284 and EP 4,251,50A.

When the liquid medium comprises organic solvent free from water, (i.e. less than 1% water by weight) in one embodiment the solvent preferably has a boiling point of from 300 to 200° C., more preferably of from 400 to 150° C., especially from 500 to 125° C.

The organic solvent may be water-immiscible, water-miscible or a mixture of such solvents. Preferred water-miscible organic solvents are any of the hereinbefore-described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether; and mixtures thereof.

When the liquid medium comprises a water-immiscible organic solvent then preferably a polar solvent is preferably included since this enhances solubility of the compound of Formula (1) in the liquid medium. Examples of polar solvents include $C_{1-4}$-alcohols.

It is especially preferred that where the liquid medium is organic solvent free from water it comprises a ketone (especially methyl ethyl ketone) and/or an alcohol (especially a $C_{1-4}$-alkanol, more especially ethanol or propanol).

The organic solvent free from water may be a single organic solvent or a mixture of two or more organic solvents. It is preferred that when the medium is organic solvent free from water it is a mixture of 2 to 5 different organic solvents. This allows a medium to be selected that gives good control over the drying characteristics and storage stability of the ink.

Liquid media comprising organic solvent free from water are particularly useful where fast drying times are required and particularly when printing onto hydrophobic and non-absorbent substrates, for example plastics, metal and glass.

The liquid media may of course contain additional components conventionally used in ink-jet printing inks, for example viscosity and surface tension modifiers, corrosion inhibitors, biocides, kogation reducing additives and surfactants which may be ionic or non-ionic.

Although not usually necessary, further colorants may be added to the composition to modify the shade and performance properties It is preferred that the composition according to the invention is ink suitable for use in an ink-jet printer. Ink suitable for use in an ink-jet printer is ink which is able to repeatedly fire through an ink-jet printing head without causing blockage of the fine nozzles.

Ink suitable for use in an ink-jet printer preferably has a viscosity of less than 20 cP, more preferably less than 10 cP, especially less than 5 cP, at 25° C.

Ink suitable for use in an ink-jet printer preferably contains less than 500 ppm, more preferably less than 250 ppm, especially less than 100 ppm, more especially less than 10 ppm in total of divalent and trivalent metal ions (other than any divalent and trivalent metal ions bound to a colorant of Formula (1) or any other component of the ink).

Preferably ink suitable for use in an ink-jet printer has been filtered through a filter having a mean pore size below 3 μm, more preferably below 31 μm, especially below 2 μm, more especially below 1 μm. This filtration removes particulate matter that could otherwise block the fine nozzles found in many ink-jet printers.

Preferably ink suitable for use in an ink-jet printer contains less than 500 ppm, more preferably less than 250 ppm, especially less than 100 ppm, more especially less than 10 ppm in total of halide ions.

Preferred compositions comprise:

(a) from 0.01 to 30 parts of compounds of Formula (1); and (b) from 70 to 99.99 parts of a liquid medium;

wherein all parts are by weight.

Preferably the number of parts of (a)+(b)=100.

The number of parts of component (a) is preferably from 0.1 to 20, more preferably from 0.5 to 15, and especially from 1 to 5 parts. The number of parts of component (b) is preferably from 80 to 99.9, more preferably from 85 to 99.5, especially from 95 to 99 parts.

Preferably component (a) is completely dissolved in component (b). Preferably component (a) has a solubility in component (b) at 20° C. of at least 10%. This allows the preparation of liquid dye concentrates that may be used to prepare more dilute inks and reduces the chance of the dye precipitating if evaporation of the liquid medium occurs during storage.

The inks may be incorporated in an ink-jet printer as a high concentration magenta ink, a low concentration magenta ink or both a high concentration and a low concentration ink. In the latter case this can lead to improvements in the resolution and quality of printed images. Thus the present invention also provides a composition where component (a) is present in an amount of 2.5 to 7 parts, more preferably 2.5 to 5 parts (a high concentration ink) or component (a) is present in an amount of 0.5 to 2.4 parts, more preferably 0.5 to 1.5 parts (a low concentration ink).

Compositions and inks according to the present invention yield prints that display a good fastness to water, ozone and light. In particular, prints prepared using these inks display excellent ozone fastness.

A second aspect of the invention provides a compound of Formula (2) and salts thereof:

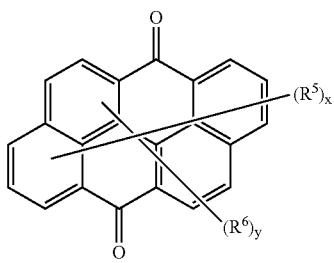

Formula (2)

wherein:
R$^5$ is selected from the group consisting of —S—R$^d$, —O—R$^d$ or —NH—R$^d$ wherein R$^d$ is optionally substituted alkyl (preferably C$_{1-4}$-alkyl), optionally substituted phenyl, optionally substituted naphthyl or optionally substituted heterocycyl;
R$^6$ is a substituent;
x is 1 to 4; and
y is 0 to 9;
provided that the compound of Formula (2) comprises at least one water solubilizing group.

R$^5$ is preferably —S—R$^d$.

R$^d$ is preferably optionally substituted phenyl.

R$^6$ may be selected from the list given for R$^1$, R$^2$, R$^3$ and R$^4$ in the first aspect of the invention.

Preferably x is 1 or 2, more preferably x is 2.

When x is greater than 1 then preferably there is no more than one R$^5$ per component ring.

When x is 2 or 4 then preferably the compound of Formula (2) is a symmetrical molecule.

Preferably y is 0 to 4, more preferably y is 0.

Thus a particularly preferred molecule of Formula (2) is of Formula (3) and salts thereof:

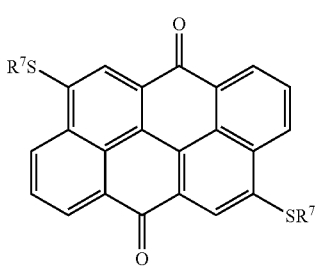

Formula (3)

wherein each R$^7$ is an optionally substituted phenyl and provided that that the compound of Formula (3) comprises at least one water solubilizing group.

Each R$^7$ may vary independently of the other, however it is preferred that each R$^7$ is the same.

Preferably the water solubilizing group is as preferred in the first aspect of the invention.

Acid and basic groups on the compounds of Formula (2), particularly acid groups, are preferably in the form of a salt. Thus, the Formulae shown herein include the compounds in free acid and in salt form.

Preferred salts are alkali metal salts, especially lithium, sodium and potassium, ammonium and substituted ammonium salts (including quaternary amines such as ((CH$_3$)$_4$N$^+$) and mixtures thereof. Especially preferred are salts with sodium, lithium, ammonia and volatile amines, more especially sodium salts. The compounds of Formula (2) may be converted into a salt using known techniques.

The compounds of Formula (2) may exist in tautomeric forms other than those shown in this specification. These tautomers are included within the scope of the present invention.

A third aspect of the invention provides a process for forming an image on a substrate comprising applying ink suitable for use in an ink-jet printer, according to the first aspect of the invention, thereto by means of an ink-jet printer.

The ink-jet printer preferably applies the ink to the substrate in the form of droplets that are ejected through a small orifice onto the substrate. Preferred ink-jet printers are piezoelectric ink-jet printers and thermal ink-jet printers. In thermal ink-jet printers, programmed pulses of heat are applied to the ink in a reservoir by means of a resistor adjacent to the orifice, thereby causing the ink to be ejected from the orifice in the form of small droplets directed towards the substrate during relative movement between the substrate and the orifice. In piezoelectric ink-jet printers the oscillation of a small crystal causes ejection of the ink from the orifice. Alternately the ink can be ejected by an electromechanical actuator connected to a moveable paddle or plunger, for example as described in International Patent Application WO00/48938 and International Patent Application WO00/55089.

The substrate is preferably paper, plastic, a textile, metal or glass, more preferably paper, an overhead projector slide or a textile material, especially paper.

Preferred papers are plain or treated papers which may have an acid, alkaline or neutral character. Glossy papers are especially preferred.

Photographic quality paper is particularly preferred.

A fourth aspect of the present invention provides a material preferably paper, plastic, a textile, metal or glass, more preferably paper, an overhead projector slide or a textile material, especially paper more especially plain, coated or treated papers printed with a composition according to the first aspect of the invention or by means of a process according to the third aspect of the invention.

It is especially preferred that the printed material of the fourth aspect of the invention is a print on photographic quality paper.

A fifth aspect of the present invention provides an ink-jet printer cartridge comprising a chamber and an ink wherein the ink is in the chamber and the ink is as defined in the first aspect of the present invention. The cartridge may contain a high concentration ink and a low concentration ink, as described in the first aspect of the invention, in different chambers.

The invention is further illustrated by the following Examples in which all parts and percentages are by weight unless otherwise stated.

EXAMPLE 1

Preparation of:

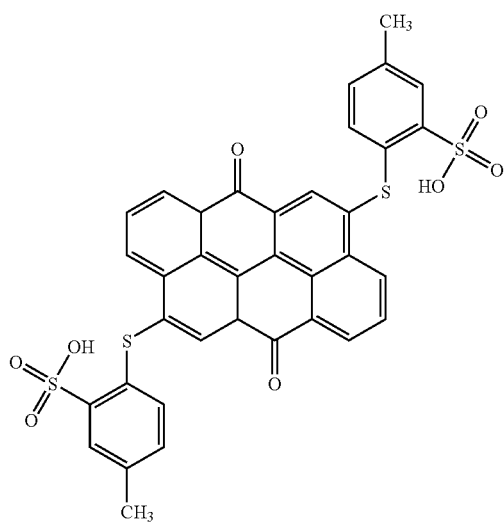

Stage 1

Preparation of:

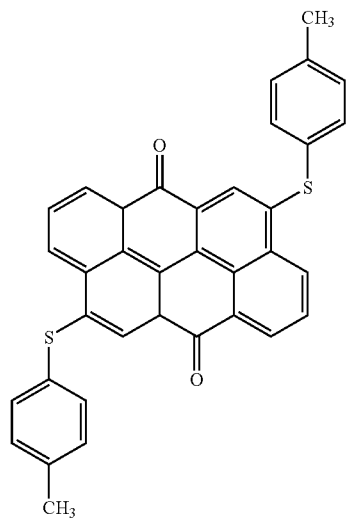

A mixture of 4-methylbenzenethiol (42.5 g) and potassium hydroxide (28.8 g) in dimethylformamide (400 ml) was stirred at 60° C. for 1 hour. Dibromoanthanthrone (40.25 g) was added portion-wise and the reaction was continued for a further 1.5 hours at 60° C. After drowning into methanol (800 ml), filtering and washing with methanol, the product was dried at 70° C. to give 44.4 g of a purple solid.

Stage 2

Preparation of the Title Compound:

The product of stage 1 (5.5 g) was added cautiously to 98% sulphuric acid (40 ml) and the resultant mixture warmed to 50° C. and stirred at this temperature for 3 hours. After cooling to room temperature the reaction mixture was added to ice and water (500 g), and the precipitated product filtered. The potassium salt of the product was prepared by dissolving in water, filtering from insoluble residue, and basifying with potassium carbonate. The crude precipitated product was separated and purified by dissolving in water and salting with potassium chloride. Removal of salts from the product was effected by dialysis, and the dialysed solution was evaporated to give 4.7 g of lustrous violet solid with a $\lambda_{max}(H_2O)$ 542 nm.

COMPARATIVE EXAMPLES

The Comparative Examples chosen represent generic examples of the type of magenta dyes currently used in ink-jet printing.

Comparative Dye Example 1 was prepared as described in Example 1 of U.S. Pat. No. 5,599,386

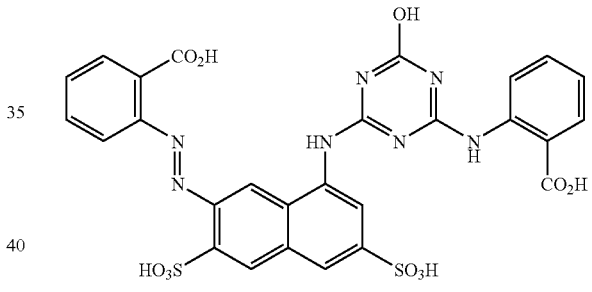

Comparative Dye Example 1

Comparative Dye Example 2 was prepared as described for Dye 101 in U.S. Pat. No. 5,824,785.

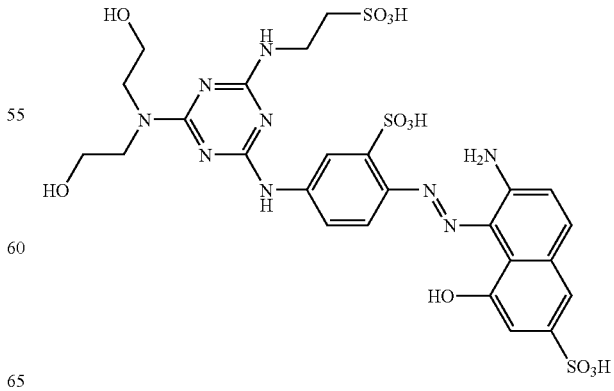

Comparative Dye Example 2

EXAMPLE 2

Preparation of Inks

Inks were prepared from the Comparative Dyes and the dye of Example 1 by dissolving 3 g of dye in 97 ml of a liquid medium consisting of 5 parts 2-pyrrolidone; 5 parts thiodiethylene glycol; 1 part Surfynol™ 465 and 89 parts water and adjusting the pH to between pH 8 to 9 with sodium hydroxide. Surfynol™ 465 is a surfactant from Air Products. Inks such as this would have a viscosity of less than 20 cP 25° C.; a surface tension in the range 20-65 dynes/cm at 25° C.; less than 500 ppm in total of divalent and trivalent metal ions (other than any divalent and trivalent metal ions bound to the colorant of or any other component of the ink); and less than 500 ppm in total of halide ions.

EXAMPLE 3

Ink-Jet Printing

Inks prepared as described above were filtered through a 0.45 micron nylon filter and then incorporated into empty print cartridges using a syringe.

These inks were then printed on to Epson Premium Glossy Photo Paper (SEC PM) and Canon Premium PR101 Photo Paper (PR101).

The prints so formed were tested for ozone fastness by exposure to 1 ppm ozone at 40° C., 50% relative humidity for 24 hrs in a Hampden 903 Ozone cabinet. Fastness of the printed ink to ozone is judged by the difference in the optical density before and after exposure to ozone.

Optical density measurements were performed using a Gretag spectrolino spectrophotometer set to the following parameters:

| | |
|---|---|
| Measuring Geometry | 45°/0° |
| Spectral Range | 380-730 nm |
| Spectral Interval | 10 nm |
| Illuminant | D65 |
| Observer | 2° (CIE 1931) |
| Density | Ansi A |
| External Filler | None |

Ozone fastness was assessed by the percentage change in the optical density of the print, where a lower figure indicates higher fastness. Results are shown in Table 1

TABLE 1

| Example | OF (SEC PM) | OF (PR 101) |
|---|---|---|
| Ink 1 | 2 | 6 |
| Comparative Ink 1 | 27 | 19 |
| Comparative Ink 2 | 81 | 69 |

Table 1 shows that a print formed with a dye/ink of the present invention has a superior ozone fastness.

Further Inks

The inks described in Tables A and B may be prepared. Numbers quoted in the second column onwards refer to the number of parts of the relevant ingredient and all parts are by weight. The inks may be applied to paper by ink-jet printing.

The following abbreviations are used in Tables A and B:
PG=propylene glycol
DEG=diethylene glycol
NMP=N-methylpyrrolidone
DMK=dimethylketone
IPA=isopropanol
MEOH=methanol
2P=2-pyrrolidone
MIBK=methylisobutyl ketone
P12=propane-1,2-diol
BDL=butane-2,3-diol
CET=cetyl ammonium bromide
PHO=$Na_2HPO_4$ and
TBT=tertiary butanol
TDG=thiodiglycol

TABLE A

| Dye Content | Water | PG | DEG | NMP | DMK | NaOH | Na Stearate | IPA | MEOH | 2P | MIBK |
|---|---|---|---|---|---|---|---|---|---|---|---|
| 2.0 | 80 | 5 | | 6 | 4 | | | | | 5 | |
| 3.0 | 90 | | 5 | 5 | | 0.2 | | | | | |
| 10.0 | 85 | 3 | | 3 | 3 | | | | 5 | 1 | |
| 2.1 | 91 | | 8 | | | | | | | | 1 |
| 3.1 | 86 | 5 | | | | | 0.2 | 4 | | | 5 |
| 1.1 | 81 | | | 9 | | 0.5 | 0.5 | | | 9 | |
| 2.5 | 60 | 4 | 15 | 3 | 3 | | | 6 | 10 | 5 | 4 |
| 5 | 65 | | 20 | | | | | 10 | | | |
| 2.4 | 75 | 5 | 4 | | 5 | | | | 6 | | 5 |
| 4.1 | 80 | 3 | 5 | 2 | 10 | | 0.3 | | | | |
| 3.2 | 65 | | 5 | 4 | 6 | | | 5 | 4 | 6 | 5 |
| 5.1 | 96 | | | | | | | | 4 | | |
| 10.8 | 90 | 5 | | | | | | 5 | | | |
| 10.0 | 80 | 2 | 6 | 2 | 5 | | | 1 | | 4 | |
| 1.8 | 80 | | 5 | | | | | | | 15 | |
| 2.6 | 84 | | | 11 | | | | | | 5 | |
| 3.3 | 80 | 2 | | | 10 | | | | 2 | | 6 |
| 12.0 | 90 | | | | 7 | 0.3 | | 3 | | | |

TABLE A-continued

| Dye Content | Water | PG | DEG | NMP | DMK | NaOH | Na Stearate | IPA | MEOH | 2P | MIBK |
|---|---|---|---|---|---|---|---|---|---|---|---|
| 5.4 | 69 | 2 | 20 | 2 | 1 | | | | | 3 | 3 |
| 6.0 | 91 | | | 4 | | | | | | 5 | |

TABLE B

| Dye Content | Water | PG | DEG | NMP | CET | TBT | TDG | BDL | PHO | 2P | PI2 |
|---|---|---|---|---|---|---|---|---|---|---|---|
| 3.0 | 80 | 15 | | | 0.2 | | | | | 5 | |
| 9.0 | 90 | | 5 | | | | | | 1.2 | | 5 |
| 1.5 | 85 | 5 | 5 | | 0.15 | 5.0 | 0.2 | | | | |
| 2.5 | 90 | | 6 | 4 | | | | | 0.12 | | |
| 3.1 | 82 | 4 | 8 | | 0.3 | | | | | | 6 |
| 0.9 | 85 | | 10 | | | | | 5 | 0.2 | | |
| 8.0 | 90 | | 5 | 5 | | | 0.3 | | | | |
| 4.0 | 70 | | 10 | 4 | | | | 1 | | 4 | 11 |
| 2.2 | 75 | 4 | 10 | 3 | | | | 2 | | 6 | |
| 10.0 | 91 | | | 6 | | | | | | 3 | |
| 9.0 | 76 | | 9 | 7 | | 3.0 | | | 0.95 | 5 | |
| 5.0 | 78 | 5 | 11 | | | | | | | 6 | |
| 5.4 | 86 | | | 7 | | | | | | 7 | |
| 2.1 | 70 | 5 | 5 | 5 | 0.1 | 0.2 | 0.1 | 5 | 0.1 | 5 | |
| 2.0 | 90 | | 10 | | | | | | | | |
| 2 | 88 | | | | | | 10 | | | | |
| 5 | 78 | | | 5 | | | 12 | | | 5 | |
| 8 | 70 | 2 | | 8 | | | 15 | | | 5 | |
| 10 | 80 | | | | | | 8 | | 12 | | |
| 10 | 80 | | 10 | | | | | | | | |

The invention claimed is:

1. A composition comprising:
   (a) a compound of Formula (1)

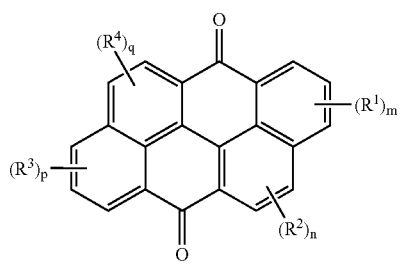

Formula (1)

wherein:
   $R^1$, $R^2$, $R^3$ and $R^4$ independently are substituents and at least one of the groups represented by $R^1$, $R^2$, $R^3$ and $R^4$ is —S—$R^c$, —O—$R^c$ or —NH—$R^c$ wherein $R^c$ is optionally substituted $C_{1-4}$-alkyl or optionally substituted phenyl;
   m and p independently are 0 to 3; and
   n and q independently are 0 to 2:
   provided that the compound of Formula (1) comprises at least one water solubilising group; and
   (b) a liquid media.

2. A composition according to claim 1 wherein the sum of m+n+p+q is 2.

3. A composition according to claim 1 wherein two of the groups represented by $R^1$, $R^2$, $R^3$ and $R^4$ are —S—$R^c$ where $R^c$ is optionally substituted phenyl.

4. A composition according to claim 1 wherein the compound of Formula (1) has a solubility in water at 25° C. of at least 1%.

5. A composition according to claim 1 wherein the compound of Formula (1) is a compound selected from the group consisting of compounds of Formula (2) and salts thereof:

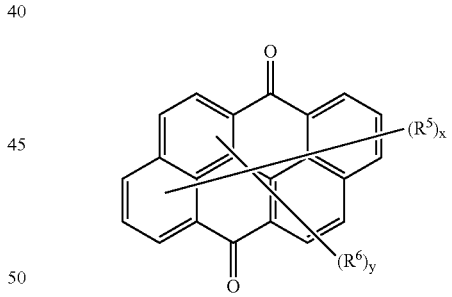

Formula (2)

wherein:
   $R^5$ is selected from the group consisting of —S—$R^d$, —O—$R^d$ or —NH—$R^d$ wherein $R^d$ is optionally substituted $C_{1-4}$-alkyl, or optionally substituted phenyl;
   $R^6$ is a substituent;
   x is 1 to 4; and
   y is 0 to 9;
   provided that the compound of Formula (2) comprises at least one water solubilizing group.

6. A composition according to claim 5 wherein the compound of Formula (2) is of Formula (3) and salts thereof:

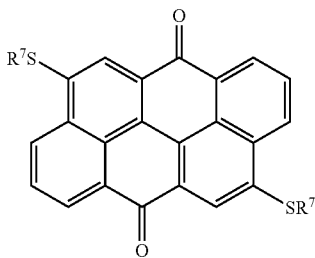

Formula (3)

wherein each R⁷ is an optionally substituted phenyl and provided that that the compound of Formula (3) comprises at least one water solubilizing group.

7. A composition according to claim 6 wherein each R⁷ is the same.

8. A composition according to claim 1 wherein the liquid media comprises a mixture of water and organic solvent.

9. An ink-jet printer ink comprising a composition according to claim 1 which is ink suitable for use in an ink jet printer.

10. A compound of Formula (2) and salts thereof:

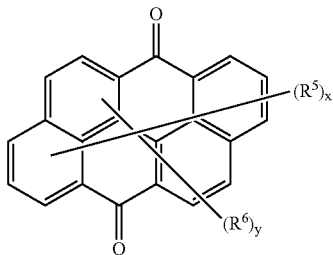

Formula (2)

wherein:
R⁵ is selected from the group consisting of —S—R$^d$, —O—R$^d$ or —NH—R$^d$ wherein R$^d$ is optionally substituted $C_{1-4}$-alkyl, or optionally substituted phenyl;
R⁶ is a substituent;
x is 1 to 4; and
y is 0 to 9;
provided that the compound of Formula (2) comprises at least one water solubilizing group.

11. A compound according to claim 10 of Formula (3) and salts thereof:

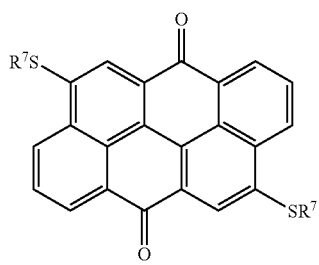

Formula (3)

wherein each R⁷ is an optionally substituted phenyl and provided that that the compound of Formula (3) comprises at least one water solubilizing group.

12. A compound according to claim 11 wherein each R⁷ is the same.

13. A process for forming an image on a substrate comprising applying ink suitable for use in an ink-jet printer, according to claim 9, thereto by means of an ink-jet printer.

14. A material printed by means of a process according to claim 13.

15. A material according to claim 14 which is a print on photographic quality paper.

* * * * *